US007838212B2

(12) United States Patent
Bjorndal et al.

(10) Patent No.: US 7,838,212 B2
(45) Date of Patent: Nov. 23, 2010

(54) APPARATUS AND METHOD FOR PROVIDING LIVE DINOFLAGELLATES FOR TOXICITY TESTS

(75) Inventors: Bryan Bjorndal, Carlsbad, CA (US); David Lapota, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 987 days.

(21) Appl. No.: 11/603,656

(22) Filed: Nov. 22, 2006

(65) Prior Publication Data

US 2008/0085549 A1 Apr. 10, 2008

Related U.S. Application Data

(63) Continuation-in-part of application No. 11/586,747, filed on Oct. 10, 2006, now abandoned, and a continuation-in-part of application No. 11/586,745, filed on Oct. 10, 2006, now Pat. No. 7,704,731.

(51) Int. Cl.
*C12N 1/10* (2006.01)
*C12N 1/04* (2006.01)
*C12Q 1/00* (2006.01)
*C12M 1/34* (2006.01)
*C12N 1/00* (2006.01)

(52) U.S. Cl. .................. 435/4; 435/243; 435/258.1; 435/260

(58) Field of Classification Search ............... 435/4, 435/243, 258.1, 260
See application file for complete search history.

(56) References Cited

U.S. PATENT DOCUMENTS 4,950,594 A * 8/1990 Stiffey .................. 435/32

OTHER PUBLICATIONS

Sabaté et al. 1995. Bioluminesence in Toxicity Testing, Journal of Environmental Geosciences, vol. 2, pp. 46-53.*
B. M. Sweeney, F. T. Haxo, and J. W. Hastings; Action Spectra for Two Effects of Light on Luminescence in Gonyaulax polyedra; The Journal of General Physiology; Nov. 1, 1959, vol. 43, pp. 285-299.
J. Woodland Hastings and Beatrice M. Sweeney; On The Mechanism of Temperature Independence in a Biological Clock; PROC. N. A. S.; Jul. 14, 1957, vol. 43, pp. 804-811.

* cited by examiner

*Primary Examiner*—Jon P Weber
*Assistant Examiner*—Kailash C Srivastava
(74) *Attorney, Agent, or Firm*—Kyle Eppele; J. Eric Anderson (57) ABSTRACT

A cartridge comprising: a container having a lower end; an aqueous suspension of dinoflagellates contained in the container; a gas port operatively coupled to the container, the port capable of directing a gas into the aqueous suspension in the lower end of the container; a gas vent operatively coupled to the container; and a shipping seal operatively coupled to the container to prevent the aqueous suspension from exiting the container.

14 Claims, 15 Drawing Sheets

APPARATUS AND METHOD FOR PROVIDING LIVE DINOFLAGELLATES FOR TOXICITY TESTS

CROSS-REFERENCE TO RELATED APPLICATIONS

This application is a continuation in part of both U.S. application Ser. No. 11/586,747, filed Oct. 10, 2006, now abandoned entitled "Method for Stimulation of Bioluminescent Organisms Via Turbulence Created by Gas Bubbles" (Parent Application 1) (Navy Case # 98122); and U.S. application Ser. No. 11/586,745, filed Oct. 10, 2006, now U.S. Pat. No. 7,704,731 entitled "System and Method for Quantifying Toxicity in Water, Soil, and Sediments" (Parent Application 2) (Navy Case # 98125). Both Parent Application 1 and Parent Application 2 are hereby incorporated by reference herein in their entirety for their teachings.

FEDERALLY-SPONSORED RESEARCH AND DEVELOPMENT

This invention was developed with federal funds and is assigned to the United States Government. Licensing and technical inquiries may be directed to the Office of Patent Counsel, Space and Naval Warfare Systems Center, San Diego, Code 20012, San Diego, Calif., 92152; telephone (619) 553-3001, facsimile (619) 553-3821. Reference Navy Case No. 98123.

BACKGROUND OF THE INVENTION

Current apparatuses and methods of providing live dinoflagellates for use in water, soil, and sediment toxicity tests typically involve time-consuming and costly on-site procedures such as maintaining stock cultures of dinoflagellates in incubators, dividing the cultures, adding new media to the cultures, and counting dinoflagellate cells with a microscope for test setup. A need exists for a quicker, less expensive method of providing live dinoflagellates to a test site for use in toxicity tests.

BRIEF DESCRIPTION OF THE DRAWINGS

Throughout the several views, like elements are referenced using like references. Figures are not drawn to scale.

DETAILED DESCRIPTION OF EMBODIMENTS

Figure 1:
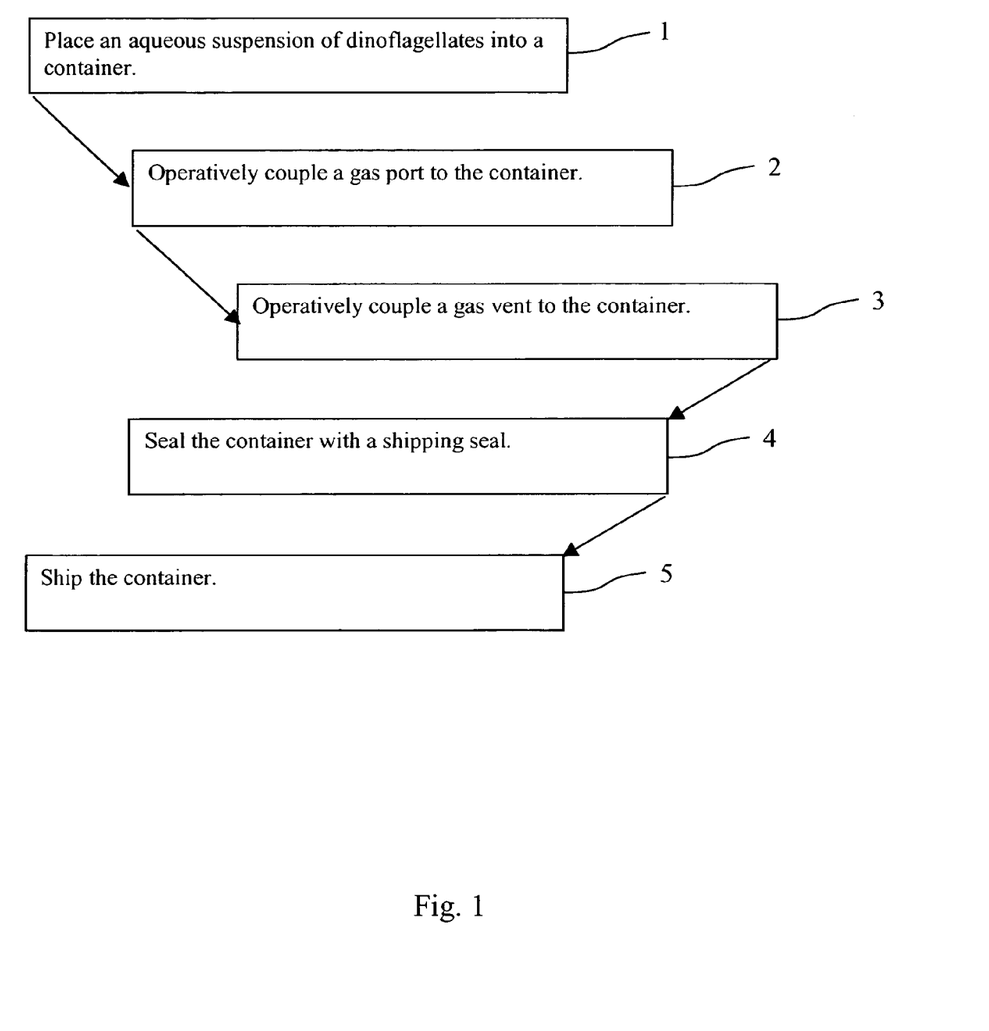
FIG. 1 is a flowchart of a method for providing live, test-quality dinoflagellates.
Figure 2:
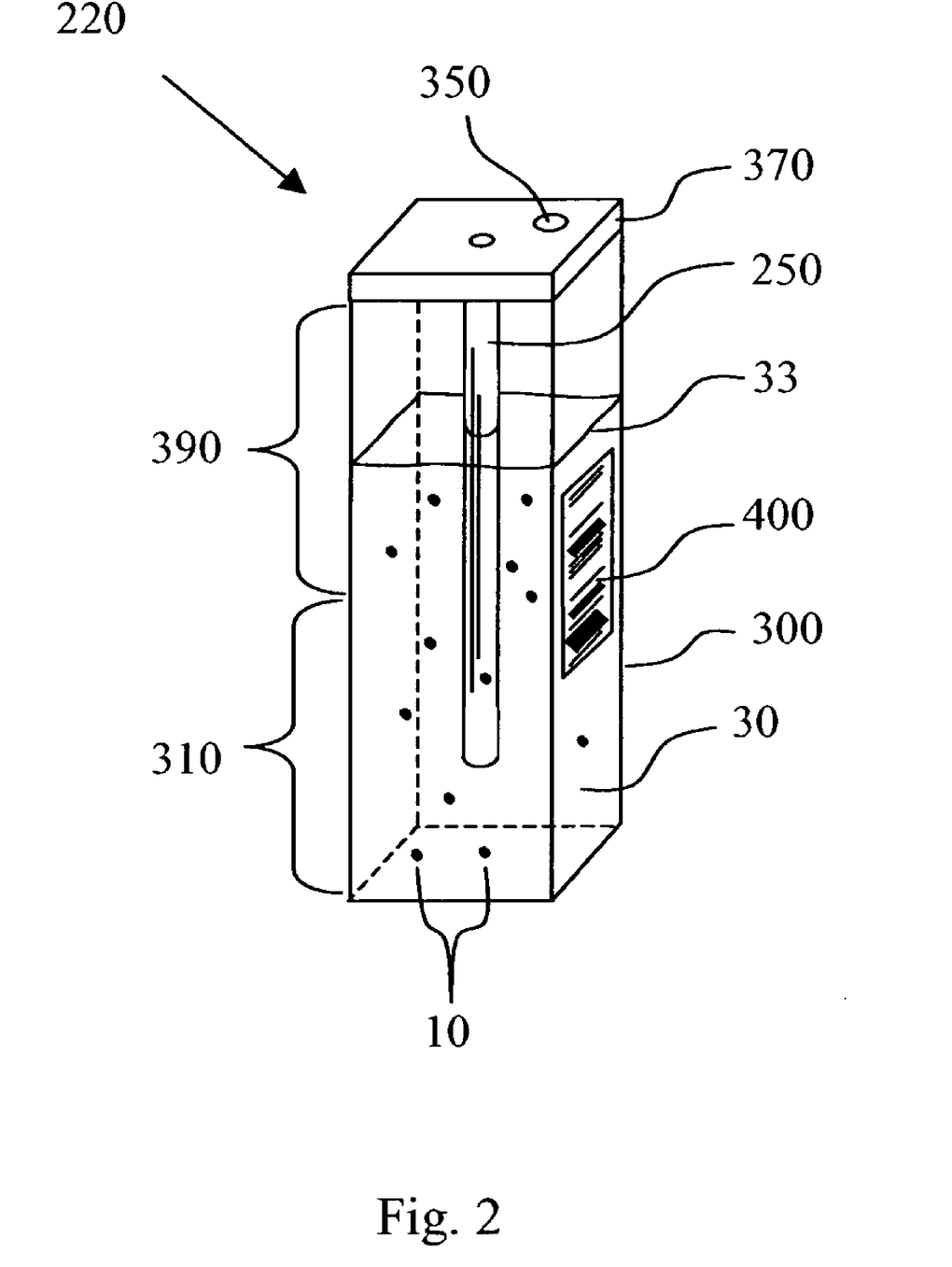
FIG. 2 shows a test-system-compatible cartridge containing dinoflagellates.
Figure 3:
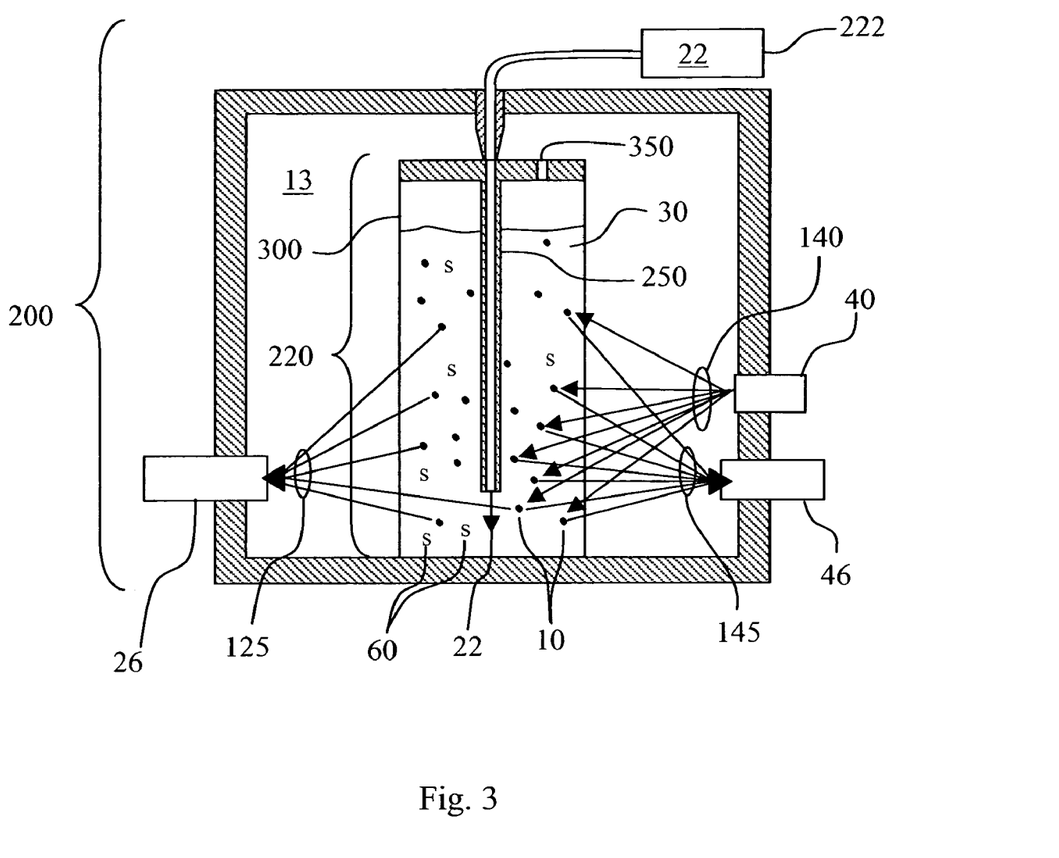
FIG. 3 shows the compatibility between a test system and a cartridge.

FIG. 1 is a flowchart of a method for using a cartridge 220, as shown in FIG. 2, to provide live, test-quality dinoflagellates 10 for substance toxicity tests. The cartridge 220 is a component of a toxicity test system 200, as shown in FIG. 3, that measures the fluorescence and bioluminescence capabilities of the dinoflagellates 10. The cartridge 220 comprises a container 300, a gas port 250, a gas vent 350, and an aqueous suspension 30. In step one, the aqueous suspension 30 that comprises dinoflagellates 10 may be placed into the container 300. In step two, the gas port 250 may be operatively coupled to the container 300. In step three, the gas vent 350 may be operatively coupled to the container 300. In step four, the container 300 may be sealed with a shipping seal 330, described below, to prevent the aqueous suspension 30 from exiting the container 300. Finally, in step five, the cartridge 220 may be shipped.

FIG. 3 illustrates the interoperability of the cartridge 220 with the toxicity test system 200. The size and shape of the cartridge 220 allow for its insertion into a light-tight test chamber 13 of the toxicity test system 200. The cartridge 220 may be coupled to the toxicity test system 200 so that a gas 22 from a gas supply 222 may be directed through the gas port 250 into the aqueous suspension 30 in container 300. When the cartridge 220 is coupled to the toxicity test system 200, the gas vent 350 is capable of allowing the gas 22 to escape from the container 300. Furthermore, the container 300 is transparent to the wavelengths of fluorescent light 145, bioluminescent light 125, and a fluorescence excitation signal 140. The container 300 is capable of containing an amount of a test sample 60 that may be added to the aqueous suspension 30. The test sample 60 may be any substance with a desired-to-be-known toxicity. Examples of the test sample 60 include, but are not limited to, soils, sediments, and water.

Figure 15:
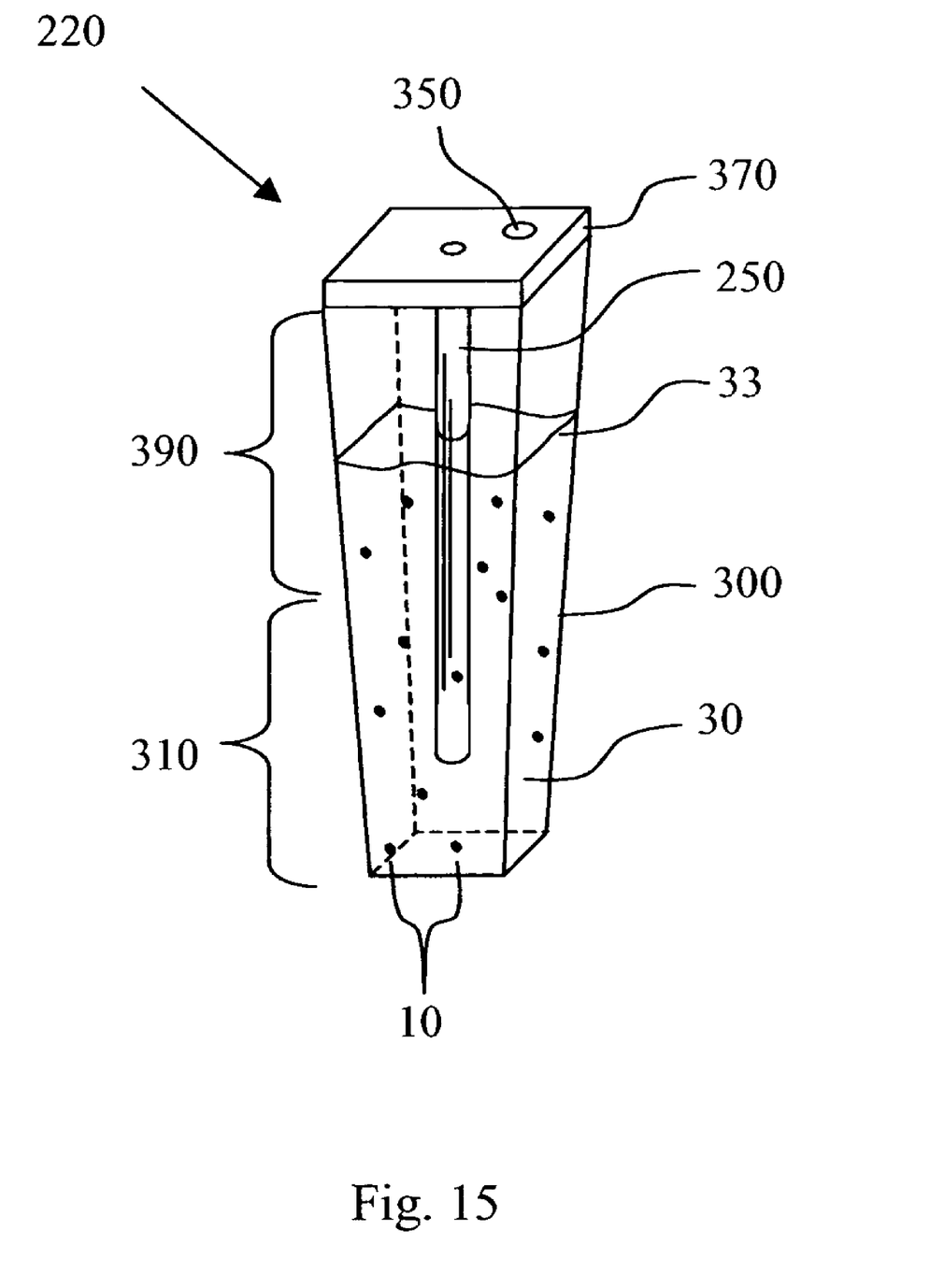
FIG. 15 shows a tapered container embodiment.

The container 300 may be made of polystyrene, glass, polycarbonate, polymethyl methacrylate, or any other material that is optically transparent to the wavelengths of the excitation signal 140, the fluorescence signal 145, and the bioluminescence signal 125. The wavelength of the bioluminescence signal 125 will generally lie within the range of about 450 to about 500 nanometers. The fluorescence signal 145 will generally lie within the range of about 300 nanometers to about 800 nanometers. Examples of the container 300 include, but are not limited to, a test tube, a cuvette, or any other container capable of fitting inside the test chamber 13, and containing aqueous suspension 30 and test sample 60. The container 300 may be made of a material that is generally chemically non-reactive with seawater, as for example, glass, acetal resin, polymethyl methacrylate, polycarbonate, or polystyrene. The container 300 has an upper end 390 and a lower end 310, as shown in FIG. 2. In one embodiment, as shown in FIG. 15, the container 300 may be tapered from the upper end 390 to the lower end 310 such that a cross section of the lower end 310 is smaller than a cross section of the upper end 390. A machine-readable label 400 may optionally be affixed to the container 300 as shown in FIG. 2.

The aqueous suspension 30 comprises dinoflagellates 10 and any medium that is capable of supporting the life of the dinoflagellates 10. Examples of such a medium include, but are not limited to, artificial seawater, enriched seawater, and natural seawater. For example, the aqueous suspension 30 may comprise dinoflagellates 10 and enriched seawater medium (ESM) according to American Society for Testing and Materials E1218-04 Standard Guide for Conducting Static Toxicity Tests with Microalgae. The interface between the aqueous suspension 30 and the atmosphere is represented in FIG. 2 as surface 33.

The dinoflagellates 10 in aqueous suspension 30 may be any species of dinoflagellates that fluoresce in response to an excitation signal 140 and emit a bioluminescence signal 125 after subjection to fluid shear-stress. The excitation signal 140 may be any signal capable of exciting the dinoflagellates 10 to emit a fluorescence signal 145. For example, the excitation signal 140 may be a continuous, optical signal with a wavelength in the range of about 420 to about 440 nanometers. Stirring, shaking, and creating turbulence with gas bubbles are a few examples of ways to introduce shear-stress-inducing pressure pulses into aqueous suspension 30 to stimulate bioluminescence emissions. Examples of embodiments of dinoflagellates 10 include, but are not limited to, *Gonyaulax polyedra, Pyrocystis lunula, Pyrocystis fusiformis*, and *Pyrodinium bahamense*. Any number of dinoflagellate cells 10 may be in the aqueous suspension 30 provided their bioluminescence and fluorescence responses are measurable. By way of example, the population density of dinoflagellates 10 may be in the range of about 1 to about 500 dinoflagellate cells per milliliter of aqueous suspension 30. For example, about 3 milliliters of aqueous suspension 30 may comprise about 600 dinoflagellates.

The gas port 250 may be any gas conduit, such as a tube or hose, that is capable of directing a sufficient amount of gas 22 into the aqueous suspension 30 in the lower end 310 of the container 300 to create bioluminescence-inducing turbulence in aqueous suspension 30. Likewise, the gas vent 350 may be any device or structure that allows gas 22 to escape from the container 300. FIG. 2 illustrates one embodiment where the gas vent 350 and the gas port 250 are integrated into a cover 370 that is mounted to the top of container 300 in a fluid tight manner. However, it is to be understood that the gas port 250 and the gas vent 350 need not be part of a cover 370, but each may be operatively coupled to any part of the container 300 individually.

Figure 4:
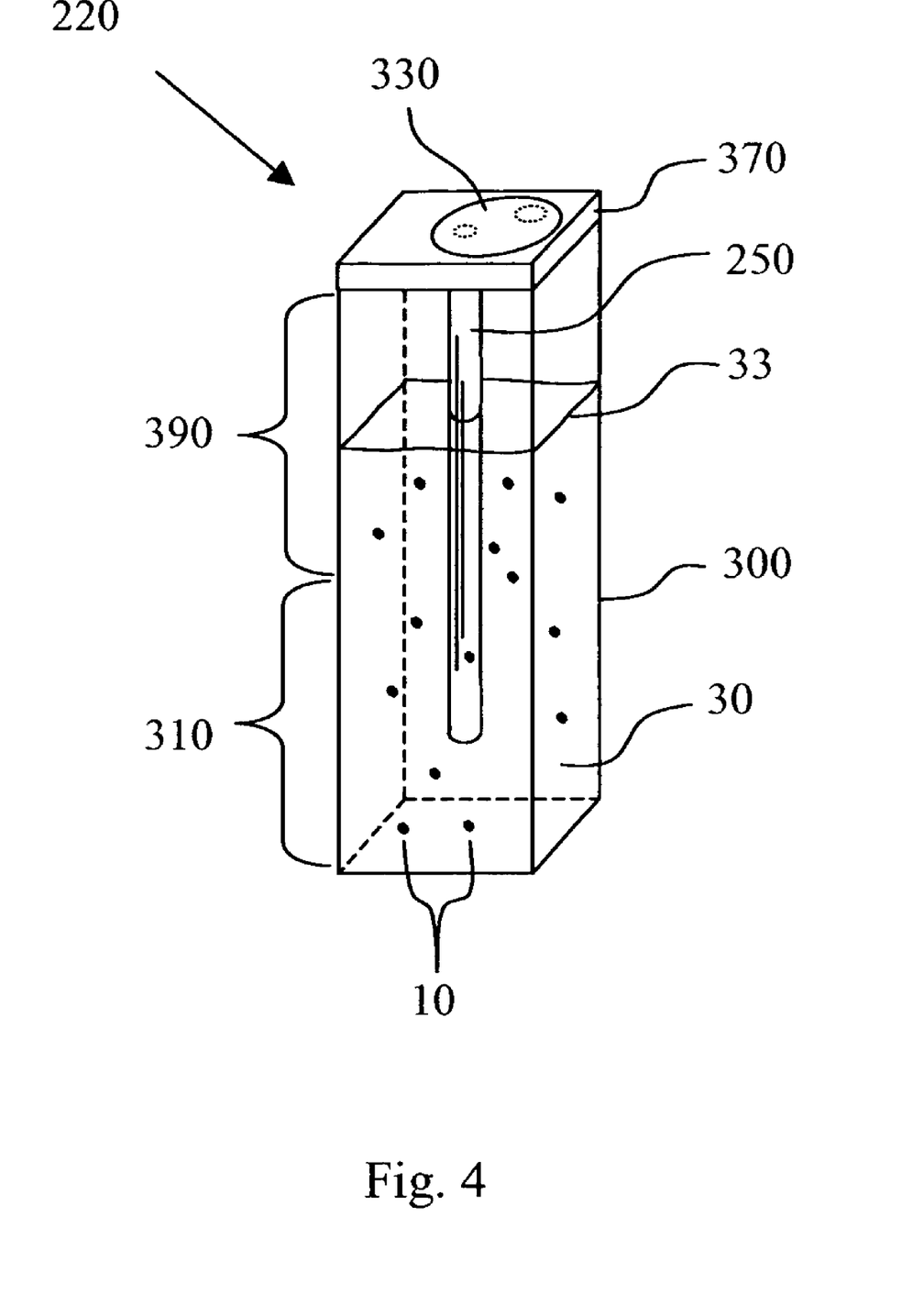
FIG. 4 shows a test-system-compatible cartridge with a shipping seal.

The shipping seal 330 may be made of any material that is capable of preventing the aqueous suspension 30 from escaping the container 300. The shipping seal may be mostly non-reactive with aqueous suspension 30 and the container 300. For example, the shipping seal 330 may be made of medical grade silicon. The shipping seal 330 may be any size or shape that is capable of sealing the container 300. FIG. 4 shows one embodiment where the shipping seal 330 is an adhesive tag that covers the gas port 250 and the gas vent 350 on the cover 370.

Figure 5:
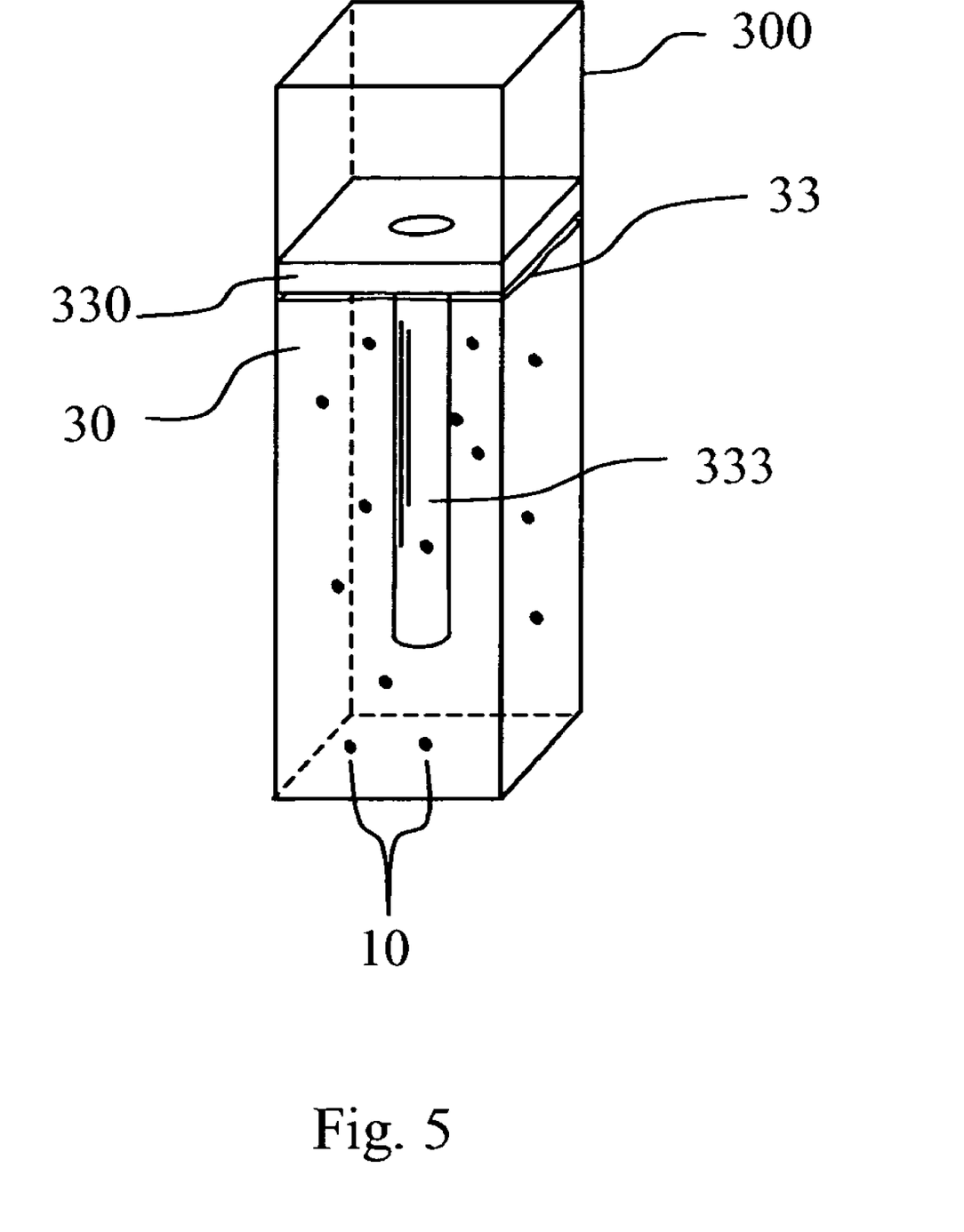
FIG. 5 shows a shipping seal positioned inside a container.

FIG. 5 shows another embodiment where the shipping seal 330 is an elastomeric plug that may be inserted into the container 300 forming a seal. For the embodiment shown in FIG. 5, the size and shape of the shipping seal 330 are such that its insertion into the container 300 creates a seal against the inner walls of the container 300—preventing the escape of aqueous suspension 30. The shipping seal 330 may be positioned adjacent to the surface 33 of the aqueous suspension 30 to reduce movement of aqueous suspension 30 inside the container 300 during shipping. Movement of aqueous suspension 30 inside the container 300 may damage the dinoflagellates 10. The shipping seal 330 may comprise a sheath 333 to enclose the gas port 250, separating the aqueous suspension 30 from the gas port 250.

Figure 6:
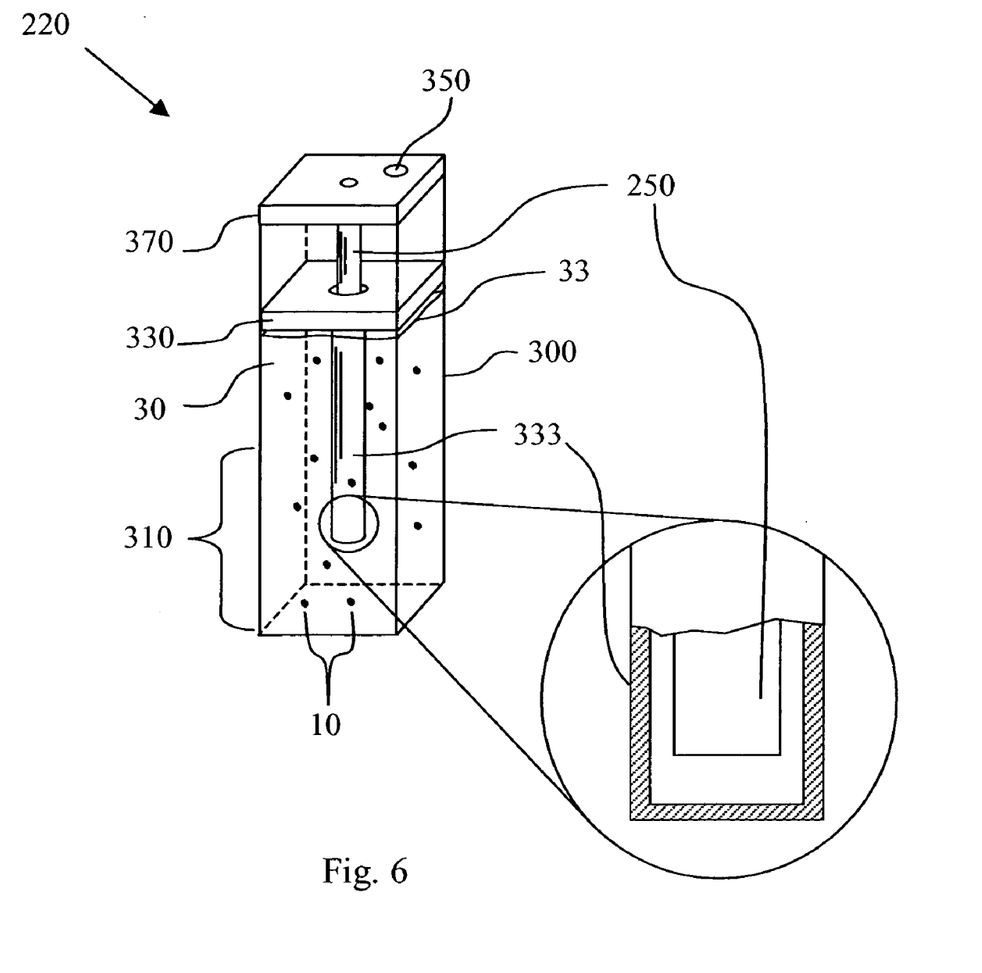
FIG. 6 shows a cartridge with an inserted shipping seal.
Figure 7:
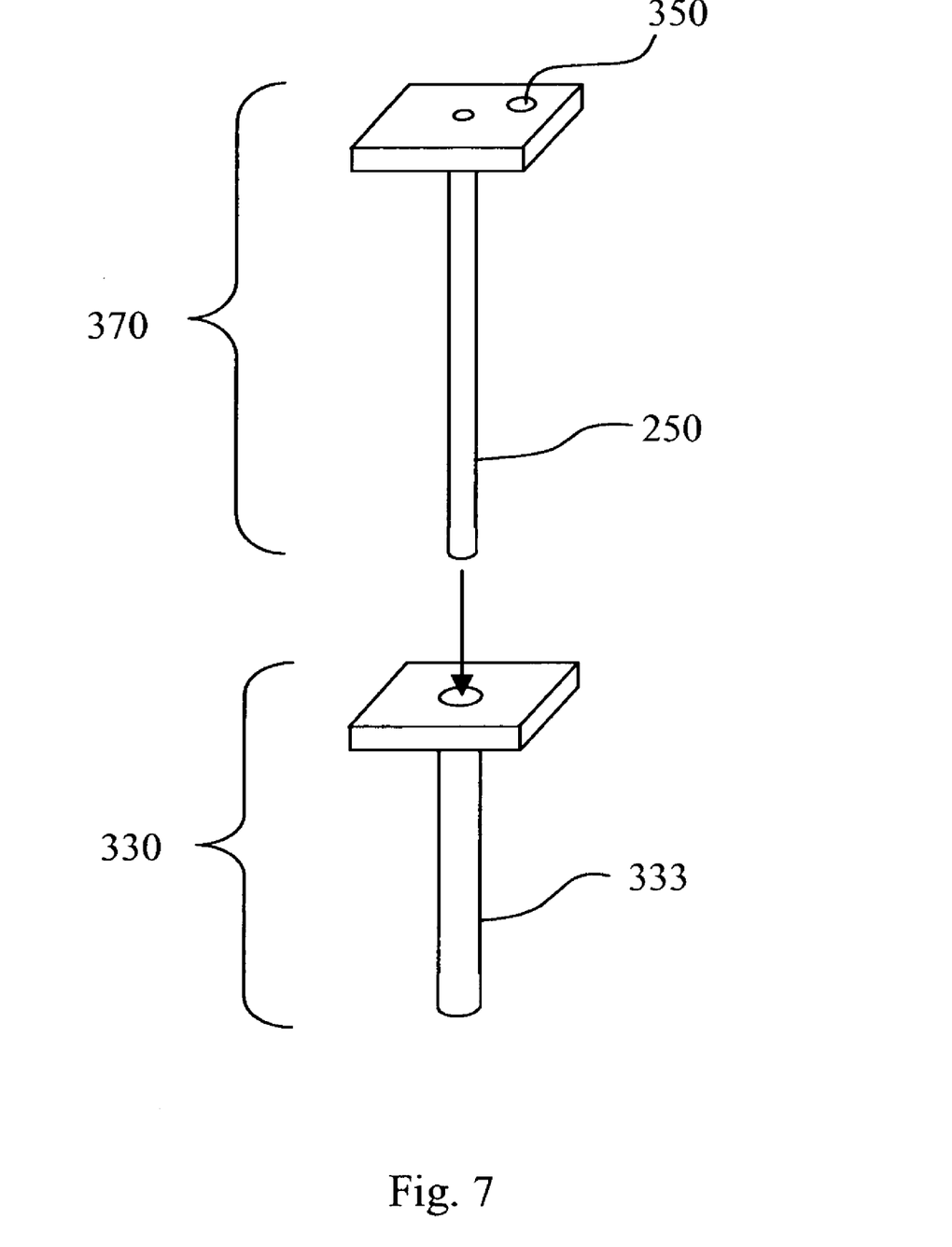
FIG. 7 shows the functional relationship between a cover and a shipping seal.

FIG. 6 and FIG. 7 illustrate the functional relationship between the cover 370 and the shipping seal 330. In the embodiment shown in FIGS. 6 and 7, the gas port 250 fits inside the sheath 333 and does not contact the aqueous suspension 30. The cartridge 220, in combination with the shipping seal 330, allows the dinoflagellates 10 contained inside the container 300 to be protected during shipping.

Figure 8:
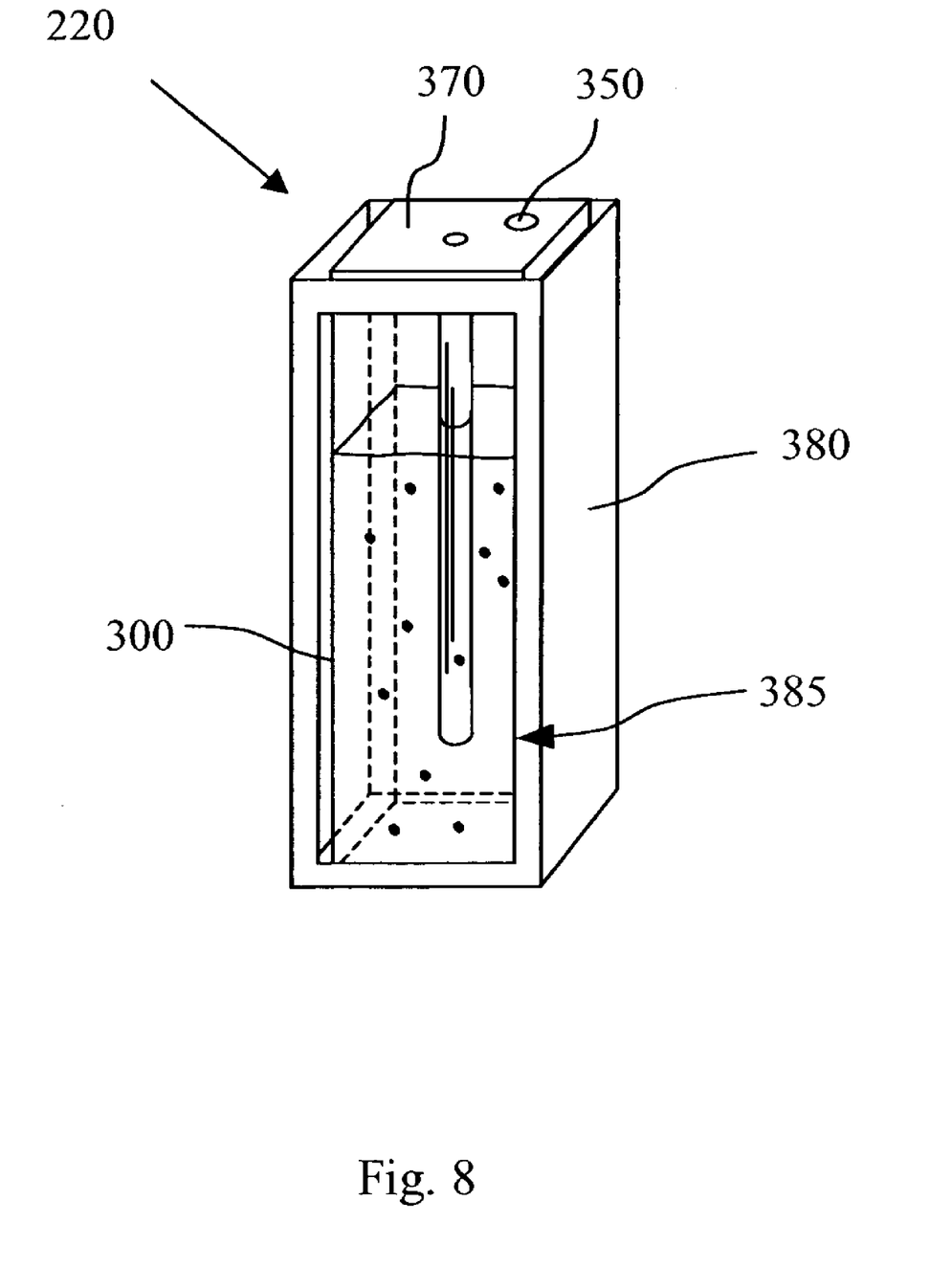
FIG. 8 shows a cartridge with an optical isolation silo.

FIG. 8 illustrates another embodiment where the cartridge 220 also comprises an optical isolation silo 380, in which the container 300 may be held. The optical isolation silo 380 is mostly optically opaque to the wavelengths of the excitation signal 140, the fluorescence signal 145, and the bioluminescence signal 125. The optical isolation silo 380 also comprises an optical window 385 through which the wavelengths of the excitation signal 140, the fluorescence signal 145, and the bioluminescence signal 125 may pass.

Figure 9:
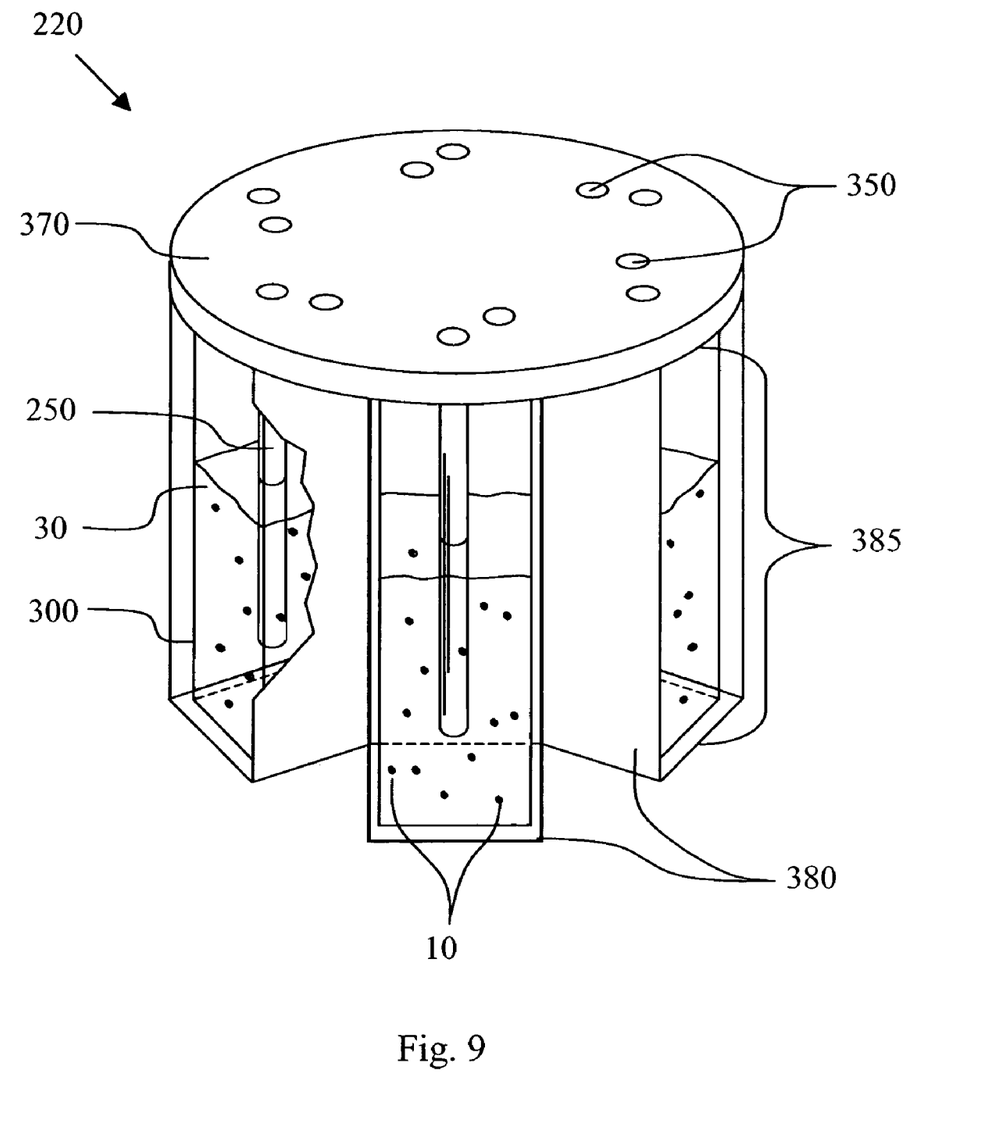
FIG. 9 shows a cartridge comprising an array of containers and optical isolation silos.
Figure 10:
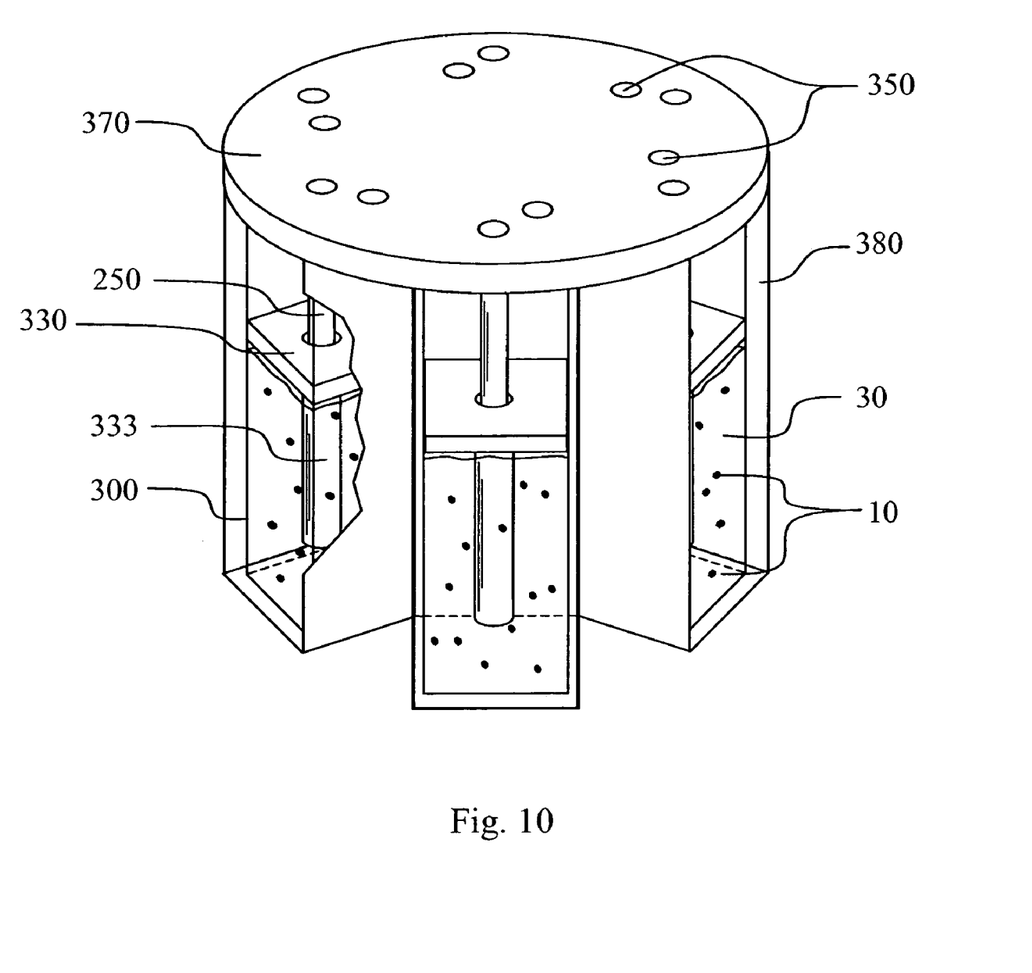
FIG. 10 shows an array of containers with shipping seals inserted.

FIG. 9 illustrates another embodiment where the cartridge 220 may comprise a plurality of containers 300, each container 300 being optically isolated from the others by an array of optical isolation silos 380. Each optical window 385 may be oriented on the optical isolation silo 380 such that optical signals entering or exiting through the optical window 385 do not impinge on containers 300 in other optical isolation silos 380. The optical isolation silos 380 may be arranged in any manner with respect to each other such that optical signals exiting an optical window 385 from one optical isolation silo 380 do not enter the window 385 of another optical isolation silo 380. FIG. 10 shows the cartridge of FIG. 9 with shipping seals 330 in each container 300.

Figure 11:
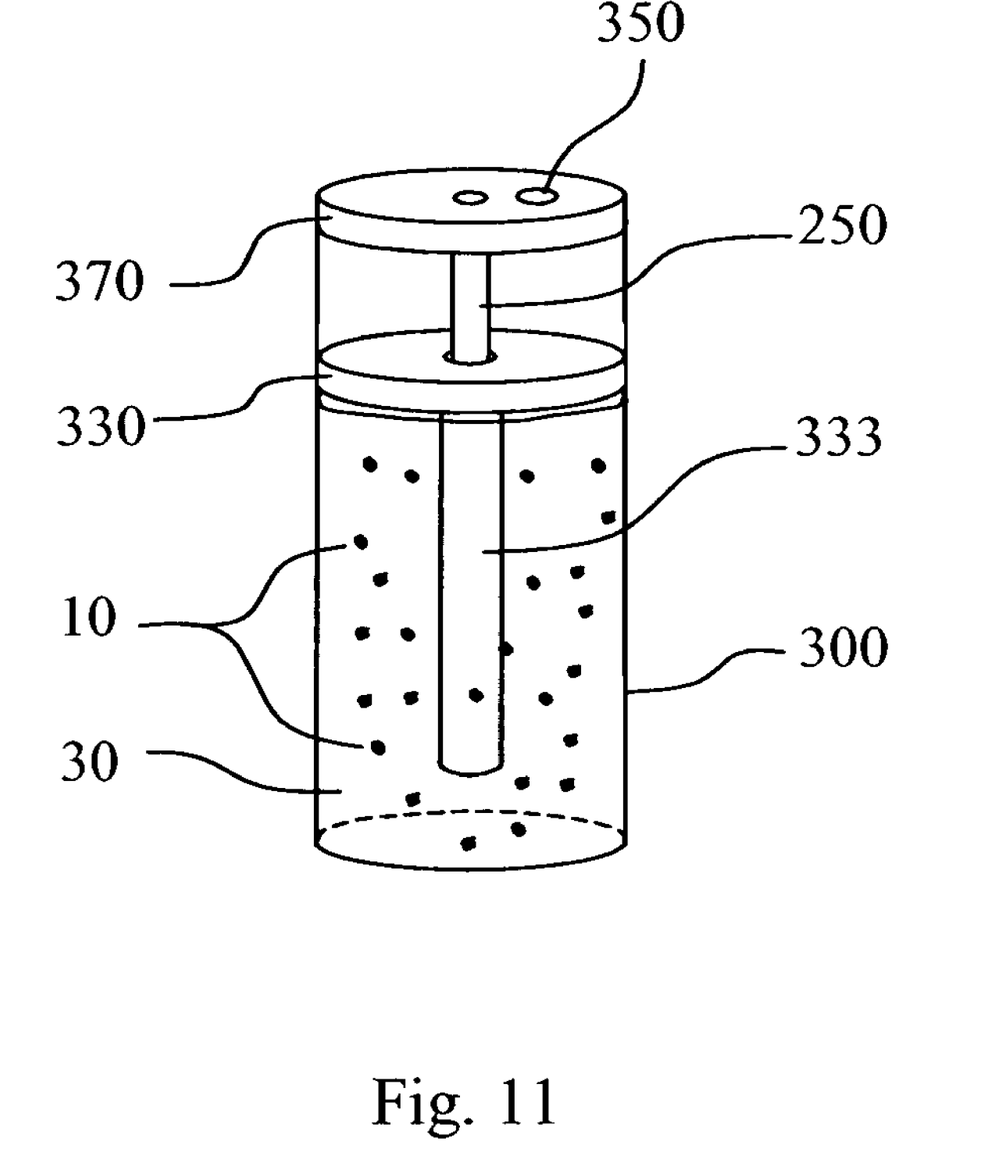
FIG. 11 shows a round container embodiment.
Figure 12:
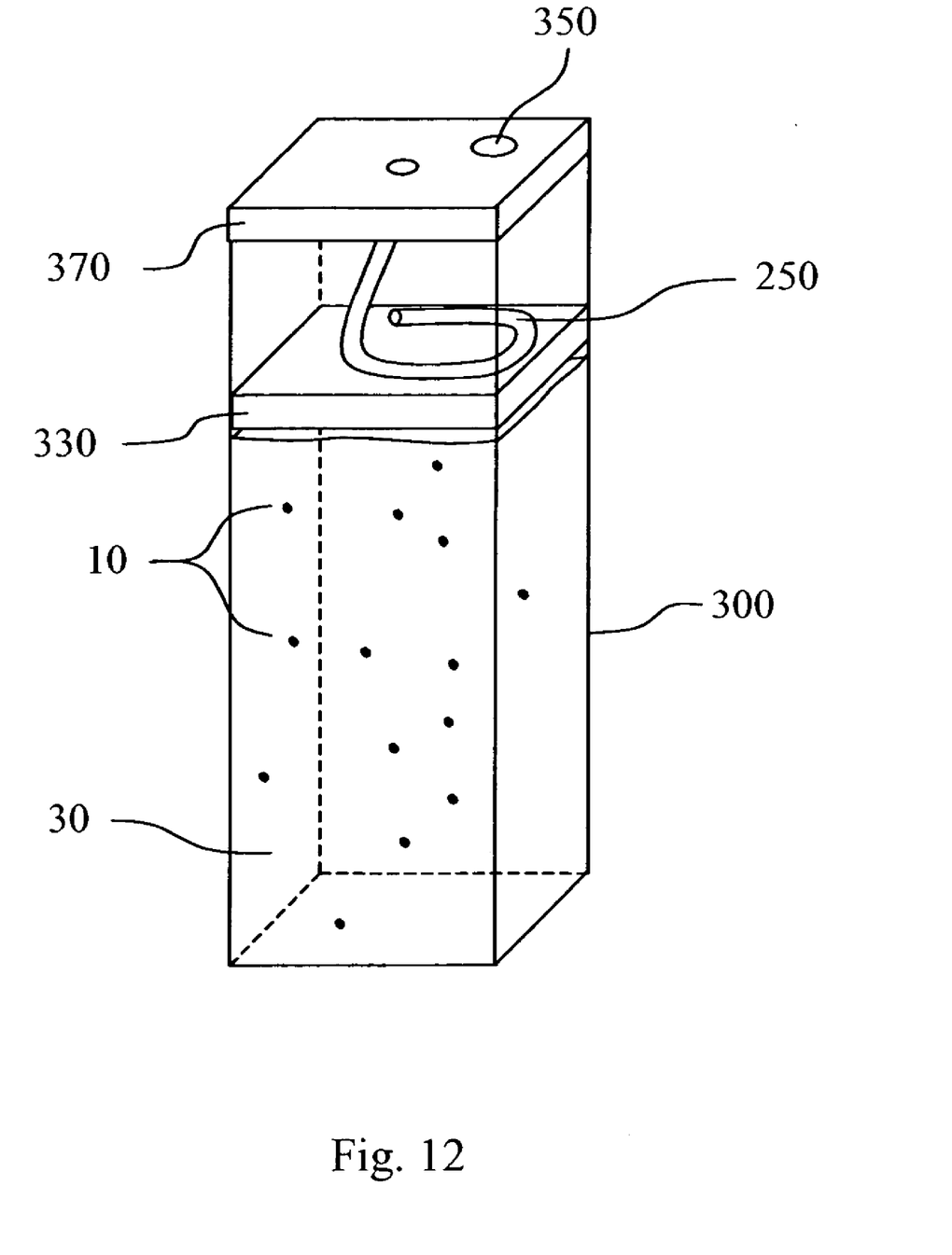
FIG. 12 shows a flexible tube embodiment.
Figure 13:
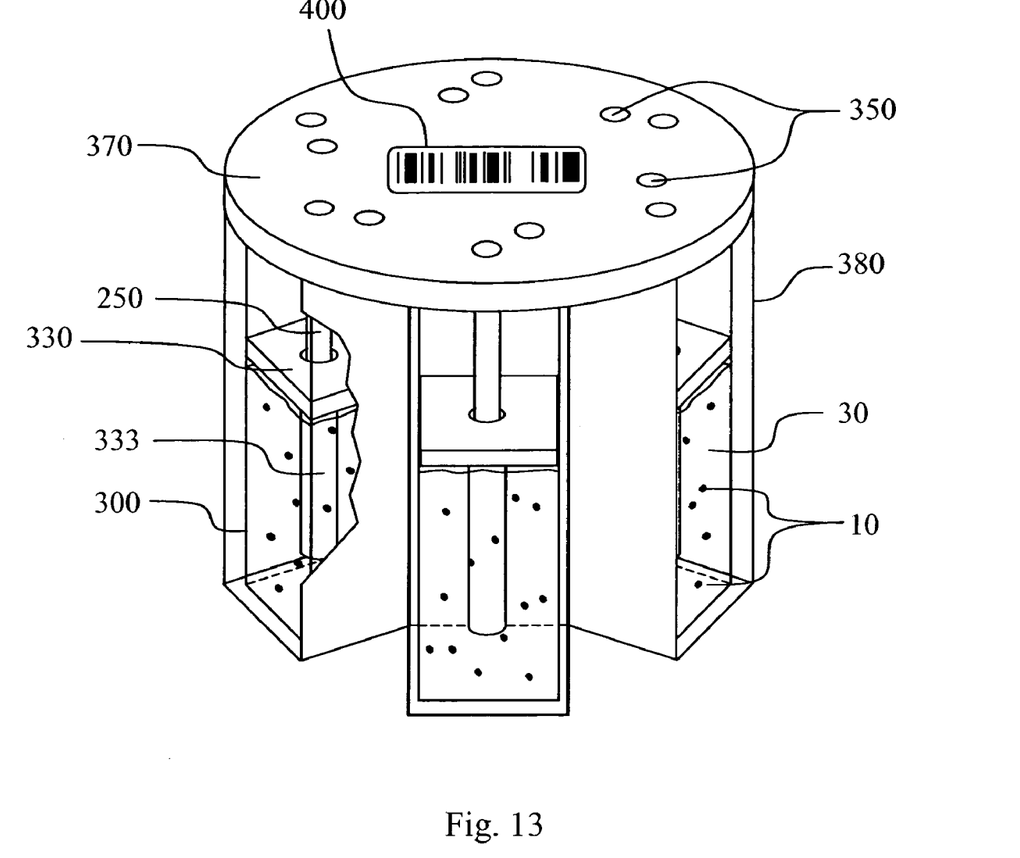
FIG. 13 shows a machine-readable identification label affixed to a cartridge.

FIG. 11 shows an alternative embodiment of the cartridge 220 where the container 300 is a round vial and the shipping seal 330 is round. FIG. 12 shows an alternative embodiment of the cartridge 220 where the gas port 250 may be a flexible tube and the shipping seal 330 has no sheath 333. FIG. 13 shows an alternative embodiment where the cartridge 220 further comprises a machine-readable identification label 400 affixed to the container 300.

Figure 14:
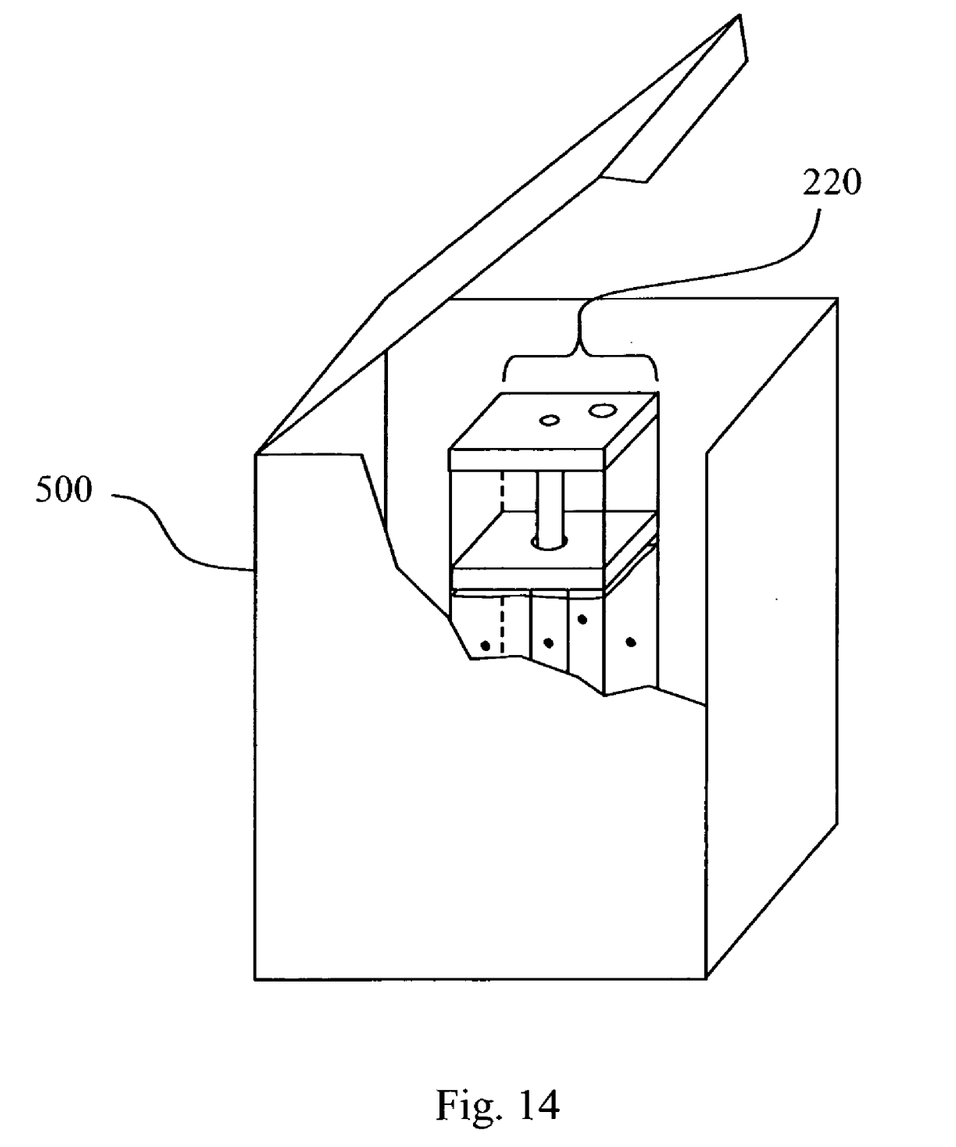
FIG. 14 shows a cartridge in a light-tight, protective shipping enclosure.

The cartridge 220 may be sealed with the shipping seal 330 and then shipped to a test site where the shipping seal 330 may be removed, the test sample 60 added to the aqueous suspension 30 and then the cartridge 220 operatively coupled to the toxicity test system 200. In the embodiment shown in FIG. 9, after shipping, the test sample 60 may be added to each of the containers 60 except for one. Prior to shipping, the cartridge 220, each container 300 sealed with a shipping seal 330, may be placed in a light-tight, protective shipping enclosure 500, as shown in FIG. 14. The shipping enclosure 500 may be mostly opaque to optical signals. Immediately prior to shipping, the dinoflagellates 10 may be exposed to about 4000 lux light for about 12 hours. Once the dinoflagellates 10 have reached their destination, they may be maintained by exposing them to alternating periods of about 12 hours of about 4000 lux light and about 12 hours of near darkness. Indirect sunlight is one example of about 4000 lux light.

From the above description of the apparatus and method for providing live dinoflagellates for toxicity tests, it is manifest that various techniques may be used for implementing the concepts of the invention without departing from its scope. The described embodiments are to be considered in all respects as illustrative and not restrictive. It should also be understood that the apparatus and method for providing live dinoflagellates for toxicity tests are not limited to the particular embodiments described herein, but are capable of many embodiments without departing from the scope of the claims.

We claim:

1. A method comprising:

placing approximately equal amounts of an aqueous suspension of bioluminescent dinoflagellates into each of a plurality of containers wherein the aqueous suspension in each of said containers comprises 1 to approximately 600 dinoflagellate cells/mL, said containers integrated into a cartridge;

attaching a gas injection port to each of said containers;

attaching a gas vent to each of said containers;

positioning shipping plugs adjacent to the surface of said aqueous suspension in each of said containers;

sealing each of said containers with one of a plurality of elastomeric shipping plugs;

exposing said dinoflagellates to an optical signal having an intensity of about 4000 lux for about 12 hours; and shipping said cartridge.

2. The method of claim 1 further comprising placing each of said cartridges into one of an array of optical isolation silos before said shipping step, wherein said cartridges are optically isolated from each other.

3. The method of claim 2, wherein said shipping step further comprises:

placing said cartridge into a light-tight, protective shipping enclosure; and shipping said enclosure.

4. The method of claim 3 further comprising:

after said shipping step maintaining said dinoflagellates by exposing said dinoflagellates to alternating periods of about 12 hours of an optical signal having an intensity of about 4000 lux and about 12 hours of darkness.

5. The method of claim 4 further comprising after said shipping step:

removing said plurality of shipping plugs and adding an amount of a test sample to all but one of said containers.

6. The method of claim 5 further comprising:

attaching said cartridge to the test sample toxicity test system after said shipping step.

7. The method of claim 6 further comprising:

after said cartridge has been attached to said toxicity test system, measuring the bioluminescence and fluorescence capabilities of said dinoflagellates in each of said cartridge to determine the toxicity of said test sample.

8. A method for providing live dinoflagellates to a test site for use in toxicity tests comprising the following steps:

placing a quantity, from 1 to approximately 600 bioluminescent dinoflaqellate cells/mL in an aqueous suspension in to each of six cuvettes at a first location that is remote from the test site, wherein each cuvette contains approximately the same number of dinoflagellate cells, wherein the cuvettes are integrated into a circular cartridge that is interoperable with a toxicity test system that is kept at the remote test site, wherein the cartridge optically isolates the cuvettes from each other;

the cartridge further comprises six gas port tubes, each gas port tube having a distal end that extends into and nearly to the bottom of a corresponding cuvette;

positioning shipping plugs adjacent to the surface of the aqueous suspension in each of the cuvettes;

sealing each of the cuvettes with an elastomeric shipping plug;

affixing a unique machine-readable identification label to the cartridge;

exposing the cartridge to an optical signal having an intensity of about 4000 lux for about 12 hours; and mailing the cartridge to the remote test site.

9. The method of claim 8, wherein each elastomeric shipping plug comprises a sheath disposed to surround the distal end of a gas port tube such that the aqueous suspension is separated from the gas port tube.

10. The method of claim 8, wherein the cartridge is mailed in a light-tight, protective shipping enclosure.

11. The method of claim 10 further comprising:

exposing the cartridge to an optical signal, having an intensity of about 4000 lux for about 12 hours after the mailing step; and exposing the cartridge to about 12 hours of darkness.

12. The method of claim 11 further comprising:

removing the shipping plugs after the mailing step and adding an amount of a test sample to all but one of the cuvettes.

13. The method of claim 12 further comprising:

attaching the cartridge to the toxicity test system after the mailing step without removing any of the aqueous suspension from the cuvettes.

14. The method of claim 13 further comprising:

testing the toxicity of the test sample after the cartridge has been attached to the toxicity test system by measuring the bioluminescence and fluorescence capabilities of the dinoflagellates in each of the cuvettes.

* * * * *